United States Patent
Matsukawa et al.

(10) Patent No.: US 8,414,500 B2
(45) Date of Patent: Apr. 9, 2013

(54) ARTERIOSCLEROSIS DIAGNOSTIC DEVICE

(75) Inventors: Mami Matsukawa, Kyoto-fu (JP); Yoshiaki Watanabe, Kizugawa (JP); Masashi Saito, Kyotanabe (JP); Takaaki Asada, Moriyama (JP); Mio Furuya, Muko (JP)

(73) Assignees: The Doshisha (JP); Murata Manufacturing Co., Ltd. (JP)

( * ) Notice: Subject to any disclaimer, the term of this patent is extended or adjusted under 35 U.S.C. 154(b) by 162 days.

(21) Appl. No.: 12/784,103

(22) Filed: May 20, 2010

(65) Prior Publication Data

US 2010/0292590 A1 Nov. 18, 2010

Related U.S. Application Data

(63) Continuation of application No. PCT/JP2008/071011, filed on Nov. 19, 2008.

(30) Foreign Application Priority Data

Nov. 20, 2007 (JP) ................. 2007-300548

(51) Int. Cl.
*A61B 5/0402* (2006.01)

(52) U.S. Cl. .................. 600/528; 600/500; 600/509

(58) Field of Classification Search .................. 600/494, 600/500, 509, 528
See application file for complete search history.

(56) References Cited

U.S. PATENT DOCUMENTS 5,830,131 A * 11/1998 Caro et al. .................... 600/300
2003/0004425 A1 * 1/2003 Narimatsu et al. ............ 600/528

FOREIGN PATENT DOCUMENTS

| JP | 3-080830 A | 4/1991 |
|---|---|---|
| JP | 07-148127 A | 6/1995 |
| JP | 09-201361 A | 8/1997 |
| JP | 2000-254104 A | 9/2000 |
| JP | 2004-135920 A | 5/2004 |
| JP | 2006-158426 A | 6/2006 |
| JP | 2006-280784 A | 10/2006 |

OTHER PUBLICATIONS

International Search Report; PCT/JP2008/071011; Dec. 16, 2008.
Japanese Office Action "Notification of Reasons for Refusal" dated May 29, 2012; Japanese Patent Application No. 2009-542567; with translation.

* cited by examiner

*Primary Examiner* — Christopher D Koharski
*Assistant Examiner* — Pamela M Bays
(74) *Attorney, Agent, or Firm* — Studebaker & Brackett PC; Tim L. Brackett, Jr.; John F. Guay

(57) ABSTRACT

An arteriosclerosis diagnostic device according to various embodiments is a simple device, resistant to an external factor, such as an error resulting from a skin surface, and capable of measuring the degree of hardness of an artery. The arteriosclerosis diagnostic device detects a heart sound and a pulse wave at least one location of a living body, the pulse wave propagating through an artery in relation to the heart sound, converts detected signals thereof into respective frequency signals, specifies the peak frequency of each of the frequency signals, and determines the degree of arteriosclerosis on the basis of the difference between the peak frequency of the heart sound and the peak frequency of the pulse wave. Accordingly, the degree of arteriosclerosis can be determined by comparison between the frequency signals.

11 Claims, 14 Drawing Sheets

[SUBJECT 1 - HEART SOUND]

(a) TIME WAVEFORM (b) WINDOW FUNCTION (c) FREQUENCY CHARACTERISTIC

[SUBJECT 2 - HEART SOUND]

(a) TIME WAVEFORM (b) WINDOW FUNCTION (c) FREQUENCY CHARACTERISTI

[SUBJECT 2 – PULSE WAVE AT WRIST]

(a) TIME WAVEFORM (b) WINDOW FUNCTION (c) FREQUENCY CHARACTERISTIC

[SUBJECT 3 - HEART SOUND]

(a) TIME WAVEFORM (b) WINDOW FUNCTION (c) FREQUENCY CHARACTERISTIC

[SUBJECT 3 - PULSE WAVE AT NECK]

(a) TIME WAVEFORM (b) WINDOW FUNCTION (c) FREQUENCY CHARACTERISTIC

[SUBJECT 3 - PULSE WAVE AT WRIST]

(a) TIME WAVEFORM (b) WINDOW FUNCTION (c) FREQUENCY CHARACTERISTIC

ARTERIOSCLEROSIS DIAGNOSTIC DEVICE

CROSS REFERENCE TO RELATED APPLICATIONS

The present application is a continuation of International Application No. PCT/JP2008/071011, filed Nov. 19, 2008, which claims priority to Japanese Patent Application No. 2007-300548 filed Nov. 20, 2007, the entire contents of each of these applications being incorporated herein by reference in their entirety.

BACKGROUND

1. Field of the Invention

The various exemplary embodiments of the claimed invention relate to an arteriosclerosis diagnostic device, and in particular, a device for estimating the elasticity of arterial walls and determining the degree of arteriosclerosis.

2. Description of the Related Art

Modern medical care is dramatically progressing from day to day. However, most of the medical care is symptomatic treatment, and research of preventive medicine, which improves self-healing power on the basis of a daily lifestyle, has hardly advanced. An example of lifestyle-related diseases is arteriosclerosis. In the existing technologies, there are various methods, such as a direct method of evaluating a blood sugar level, cholesterol, and other components from a blood sample or a urine sample, and indirect method of estimating a disease in the body from a measured value of a blood pressure, pulsation, heartbeat, or respiratory sound. However, these techniques are insufficient in terms of monitoring of biometric information.

Japanese Unexamined Patent Application Publication No. 9-201361 proposes an arteriosclerosis diagnostic device that transmits and receives an ultrasonic beam to and from an object, obtains an echo signal, measures a time difference of arrival from a distance between two measurement locations, and calculates a pulse-wave propagation velocity. The device is intended to be used in diagnosis for arteriosclerosis by associating the above-mentioned calculated pulse-wave propagation velocity with the hardness of blood vessels.

However, the device described in Japanese Unexamined Patent Application Publication No. 9-201361 can obtain only the propagation velocity of a pulse wave propagating along an arterial wall (i.e., only displacement information), so there is a problem in that it is susceptible to external factors, such as an error resulting from a skin surface. Also, a calculated value is affected by the distance between two measurement locations. Hence, measurement widely varies among parts used in measurement. Furthermore, there exists a problem of the complexity and expensiveness of the measurement device.

SUMMARY

The embodiments consistent with the claimed invention provide an arteriosclerosis diagnostic device having a simple structure, being resistant to external factors, such as an error resulting from a skin surface, and being capable of measuring the degree of hardness of an artery.

In an embodiment and a first aspect consistent with the claimed invention provides an arteriosclerosis diagnostic device including first detection means for detecting a heart sound, second detection means for detecting a pulse wave in at least one location of a living body, the pulse wave propagating through an artery in relation to the heart sound, means for converting detection signals detected by the first and second detection means into their respective frequency signals, and means for determining the degree of arteriosclerosis by comparing the frequency signal of the heart sound and the frequency signal of the pulse wave.

A second aspect consistent with the claimed invention provides an arteriosclerosis diagnostic device including first detection means and second detection means for detecting pulse waves in at least two locations of a living body, respectively, the pulse waves propagating through arteries in relation to a same heartbeat, means for converting detection signals detected by the first and second detection means into respective frequency signals, and means for determining the degree of arteriosclerosis by comparing the frequency signals.

The present embodiment focuses on the relationship between viscoelasticity of an arterial wall and a transient response of a pulse wave occurring when a heartbeat propagates through a blood vessel inside the body to a distal organ. Heart sounds are vibrations of the heart accompanying diastole and systole. Pulse waves are oscillating waves in which oscillations in the aorta caused by heartbeats propagate along an arterial wall. When a blood vessel is regarded as a pipe, the characteristic of the pipe for propagating the frequency of oscillating waves vary with the viscoelasticity of the pipe. For a blood vessel having high viscoelasticity, a decrease in frequency is large. In contrast, for a blood vessel with advanced arteriosclerosis, a decrease in frequency is small.

Thus, in the first aspect consistent with the claimed invention, a heart sound and a pulse wave are synchronously detected first by detection means. That is, a heart sound and a pulse wave related to the heart sound are detected. The heart sound can be detected at a position in the vicinity of the heart, such as the chest. The pulse wave may preferably be detected at a part remote from the heart, such as the neck, wrist, or ankle. The detected signals are time-domain signals, and the signals are converted into frequency-domain signals (frequency spectrum). Then, the frequency signal in the heart sound and the frequency signal in the pulse wave are compared. In the case of a person who does not have advanced arteriosclerosis, arteries have high viscoelasticity, so the difference between the frequency signal in the heart sound and that in the pulse wave is large. In contrast, in the case of a person with advanced arteriosclerosis, the difference between the frequency signal in the heart sound and that in the pulse wave is relatively small. Therefore, the degree of arteriosclerosis can be determined by comparison between the frequency signals.

There are various frequency signals contained in a heart sound and a pulse wave, and each of the frequency signals always has a peak frequency or a center frequency. A peak frequency is a frequency at which the spectral strength or amplitude is at the maximum value. A center frequency is a frequency at the center of the spectrum. If the spectral distribution is symmetrical, the peak frequency and the center frequency are the same. If plural kinds of peaked waves are present, it is preferable that the position of a peaked wave including the maximum value be the peak frequency. For example, when a heart sound and a pulse wave at a wrist are measured, the degree of arteriosclerosis of an artery connecting the heart and the wrist can be determined by comparison between the peak frequency or the center frequency obtained at the chest and the peak frequency or the center frequency obtained at the wrist. Unlike displacement information or pressure information, frequency information is not influenced by skin at a measurement location, so a stable measurement result is obtainable.

In the first aspect, a heart sound and a pulse wave are compared. In the second aspect, diagnosis for arteriosclerosis is carried out by comparison between pulse waves propagating through arteries in at least two locations of a human body. In this case, it is necessary that two detection means detect pulse waves that propagate through arteries in relation to the same heartbeat. It is to be noted that, preferably, the distance from the heart to one detection means may differ from that to the other detection means. For example, one detection means may be near to the heart, and the other may be remote from the heart.

It is also possible to determine the degree of arteriosclerosis by detecting both pulse waves and finding the difference or ratio between their respective peak frequencies.

A process for comparing frequencies may include finding the difference between the peak frequency at a first detection location and that at a second detection location. For example, when a heart sound and a pulse wave are detected, for a healthy person who does not have arteriosclerosis, arteries have high viscoelasticity, so the peak frequency difference is large. In contrast, for a person with arteriosclerosis, arteries are hard, so the peak frequency difference is small. Accordingly, the degree of arteriosclerosis can be determined on the basis of the magnitude of the peak frequency difference.

Alternatively, the ratio of the peak frequency at one of the detection locations to the peak frequency at the other detection location may also be found. For example, when a heart sound and a pulse wave are detected, for a person with arteriosclerosis, the frequency ratio is closer to one, compared with a healthy person.

In finding the peak frequency difference or the peak frequency ratio, pulse waves at two different locations on a human body may be used without the use of a heart sound. Additionally, the ratio between the difference between the peak frequency of a heart sound and the peak frequency of a pulse wave at a part (e.g., wrist) and the difference between the peak frequency of the heart sound and the peak frequency of a pulse wave at a different part (e.g., ankle) may be found, or, alternatively, the value obtained by dividing the difference between the peak frequency of a heart sound and that of a pulse wave at a part (e.g., wrist) by the peak frequency of the heart sound may be found. These characteristic values are unique to the individual.

Finding one or more of the above-described characteristic values for a plurality of subjects, referring to other checkup data of the subjects (e.g., blood sugar level, blood pressure, total cholesterol, neutral fat, HDL cholesterol, the presence/absence of obesity, X-ray inspection, funduscopy, electrocardiography), and generating statistical data of them enable the degree of arteriosclerosis to be determined with higher precision. The status of arteriosclerosis is deemed to vary with a lifestyle, so changes in peak frequency difference over time measured by monitoring everyday life can contribute to an evaluation of the lifestyle.

Types of arteriosclerosis include atherosclerosis, arteriolosclerosis, and medial sclerosis. Arteriolosclerosis is a symptom in which a distal thin artery gradually loses flexibility in response to a continuous contraction stimulus thereto due to, for example, smoking. Atherosclerosis is a symptom in which a protuberance (plaque) is formed due to deposition of, for example, cholesterol in blood on the inner walls of blood vessels. The diagnostic method of the present invention focuses on the propagation characteristics of a pulse wave propagating along the arterial walls, and this method is useful, especially in diagnosis for arteriolosclerosis and medial sclerosis.

A heart sound contains a first sound component accompanying systole and a second sound component accompanying diastole, and a pulse wave also contains a constituent associated with the first sound component and a constituent associated with the second sound component. In this specification, for the sake of convenience, the constituent associated with the first sound component and the constituent associated with the second sound component of the pulse wave are also referred to as the first sound component and the second sound component, respectively.

Although both the first sound component and the second sound component are detectable by detection means, it is preferable that the first sound component be extracted because the first sound component is clearly detectable independently of the measurement part.

A process for extracting only the first sound component from a heart sound and a pulse wave may include multiplying a detection signal output from detection means by a window function, for example.

Frequency-converting the extracted first sound component by using conversion means, such as a fast Fourier transform (FFT), enables the obtainment of a frequency spectrum of the first sound component. Extracting only the first sound component by use of the window function can shorten the processing time required for frequency conversion and avoid it from being mixed with other sounds; hence, sufficient stability of measurement can be maintained. It is to be noted that the process for extracting only the first sound component may include some other processes, other than the one using the window function.

The detection means included in the diagnostic device according to the present invention may be any means as long as it can detect a heart sound and a pulse wave. However, it is preferable that detection device or method for detecting a heart sound or a pulse wave as displacement information (e.g., the amount of displacement or displacement velocity) be used. For example, if a piezoelectric transducer is used, a heart sound and a pulse wave are detectable as a displacement velocity signal, and compactness and cost-effectiveness are achieved.

In addition, a heart sound and a pulse wave are detectable by simply making the piezoelectric transducer, for example, be in contact with the surface of the skin of a human body, such that the condition of arteriosclerosis can be diagnosed easily without causing injury or pain. Furthermore, directly measuring oscillations of a pulse wave (displacement information), not measuring a pulse pressure with a traditional sphygmograph, enables a heart sound and a pulse wave to be measured more easily and more accurately. If the same model of piezoelectric transducers are used as the detection means for detecting a heart sound and the detection means for detecting a pulse wave (or that for a pulse wave and that for another pulse wave), variations in signal characteristics detected by the transducers can be reduced, and errors occurring in comparison of peak frequencies can also be reduced.

As described above, with the first aspect consistent with the claimed invention, detection signals in a heart sound and in a pulse wave are frequency-converted, and diagnosis for arteriosclerosis is carried out on the basis of information on the frequencies. Therefore, a stable measurement result that is not influenced by skin at a measurement location is obtainable. Unlike existing technologies, there is no need to calculate a pulse-wave propagation velocity from the distance between measurement locations and the time difference between arrival of the pulse wave at one location and that at the other location, and the degree of arteriosclerosis can be estimated by simply comparing the frequency of a heart sound with the frequency of a pulse wave detected in at least one location of a human body. Accordingly, diagnosis for arteriosclerosis can be carried out with a simple device.

According to the second aspect consistent with the claimed invention, pulse waves that are propagating through arteries and that are detected in at least two locations of a human body are used to carry out diagnosis for arteriosclerosis. Accordingly, even if no heart sound is detectable, diagnosis for arteriosclerosis can be carried out, in the same way as in the first embodiment.

Other features, elements, characteristics and advantages of the embodiments consistent with the claimed inventions will become more apparent from the following detailed description with reference to the attached drawings.

DETAILED DESCRIPTION

Various embodiments consistent with the claimed inventions are described below on the basis of examples.

EXAMPLE 1

Figure 1:
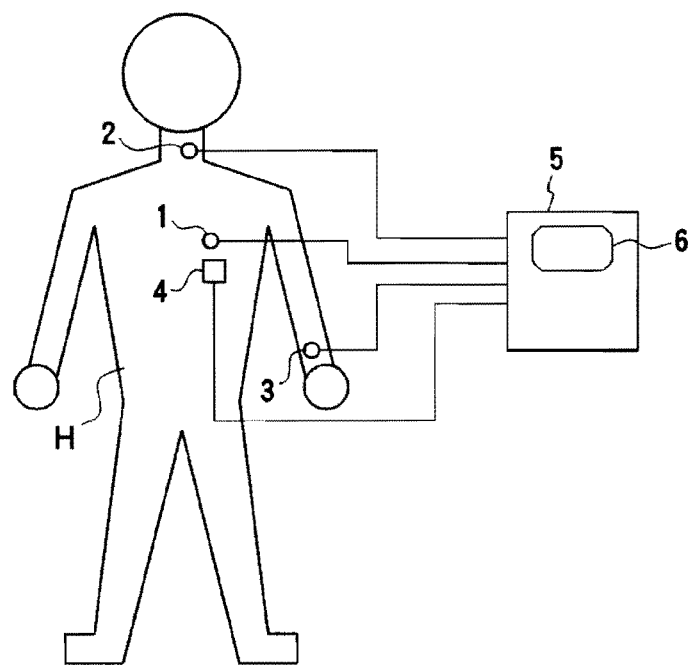
FIG. 1 is a system diagram of one example of an arteriosclerosis diagnostic device according to an embodiment.

FIG. 1 illustrates an example of an arteriosclerosis diagnostic method according to the present invention. This example is one in which diagnosis for arteriosclerosis is carried out by measurement of a heart sound and pulse waves at two locations of a human body. Referring to FIG. 1, three piezoelectric transducers 1 to 3 are attached so as to be in contact with the skin of a patient H. Each of the piezoelectric transducers 1 to 3 is a kind of an acoustic sensor that converts a heart sound and a pulse wave propagating through an artery into electrical signals indicating displacement velocities. As the contact locations of the piezoelectric transducers 1 to 3, a part at which a heart sound is detectable, such as the chest, and parts at which pulse waves propagating through arteries of the neck and the wrist are detectable, are selected. Preferably, the contact locations may be fixed. The measurement locations are not limited to those described above.

The measurement may be made at other parts, such as an elbow, ankle, waist, femoral region, and shoulder, and the number of the measurement locations may be more than three.

In addition to the piezoelectric transducers 1 to 3, an electrocardiograph 4 is attached to the chest. The piezoelectric transducers 1 to 3 and the electrocardiograph 4 are connected to a diagnostic device 5 with wiring. The diagnostic device 5 is provided with a display unit 6 for displaying a result of the diagnosis. The display unit 6 displays the degree of arteriosclerosis using a numerical value, symbol, graph or other elements.

Figure 2:
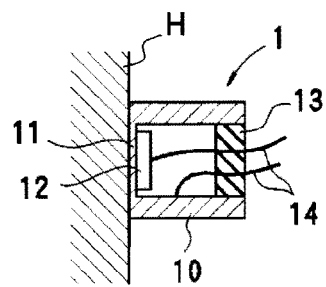
FIG. 2 is a schematic cross-sectional view of one example of a piezoelectric transducer.

FIG. 2 illustrates an example of the piezoelectric transducer 1 shown in a cross-sectional view. The other transducers 2 and 3 have the same structure as that of the piezoelectric transducer 1. The transducer 1 has a piezoelectric unimorph structure. A cylindrical casing 10 has a flat bottom 11, and the bottom 11 is configured as a vibrating surface. A piezoelectric element 12 is fixed on the inner surface of the bottom 11. The outer surface of the bottom 11 is in contact with the skin of the patient H. The opening of the casing 10 is closed by a seal 13, and leads 14 are drawn out through the seal 13. It is to be noted that the structure of the piezoelectric transducer is not limited to that illustrated in FIG. 2.

Figure 3:
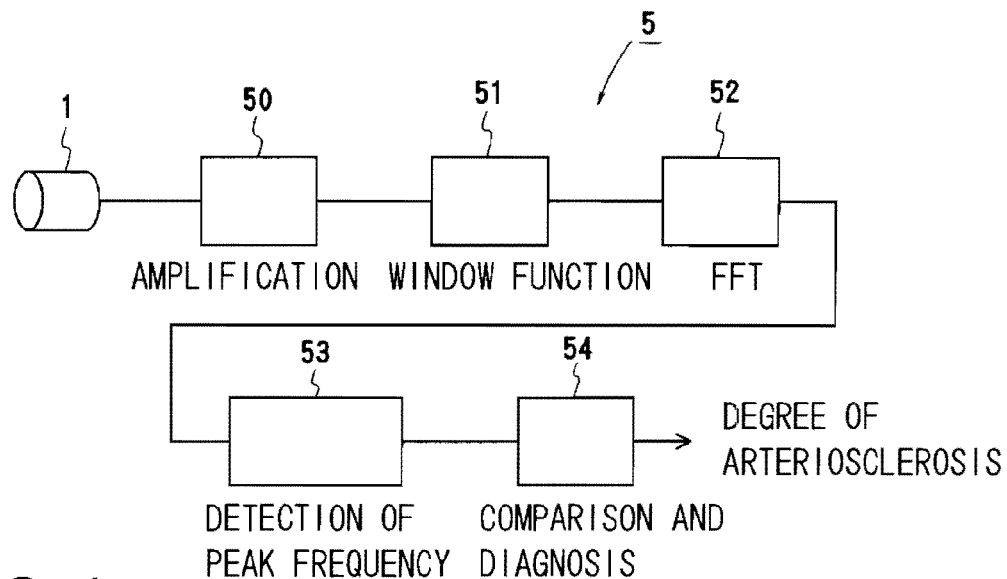
FIG. 3 is an internal circuit diagram of the diagnostic device according to an embodiment.

FIG. 3 illustrates an internal circuit configuration of the diagnostic device 5. A detection signal detected by the piezoelectric transducer 1 is amplified by an amplifier 50 and then input into a block 51. In the block 51, the input detection signal is multiplied by a window function so that only a first sound component can be extracted from the detection signal. In a block 52, the extracted first sound component is converted into a frequency signal, for example, by a fast Fourier transform (FFT). However, another converting process other than FFT can also be used.

The frequency signal obtained by the conversion is sent to a block 53. In the block 53, the peak frequency of a heart sound is detected. Similarly, the peak frequency of a pulse wave related to the heart sound at the neck and that at a wrist are detected by the piezoelectric transducers 2 and 3, which are not shown in FIG. 3. A peak frequency is a frequency at which the spectral strength (or amplitude) is at the peak value. Then, in a block 54, the peak frequency of the heart sound and the peak frequency of each of the pulse waves are compared, and the degree of arteriosclerosis of a subject is thus obtained.

It is to be noted that an output signal of the electrocardiograph 4 showing an electrical waveform of heartbeats may be connected to the diagnostic device 5 and it may be used in identifying the first sound component of a heart sound and the first sound component of a pulse wave.

Next, results of diagnosis using the above diagnostic method on three subjects 1 to 3 are described. Subject 1 is a 23-year-old male who does virtually no physical activity. Subject 2 is a 23-year-old male who plays tennis on a regular basis. Subject 3 is a 60-year-old male who has an age-related degree of arteriosclerosis according to regular medical checkup records and has blood vessels slightly containing calcium.

-- Subject 1 --

Figure 4:
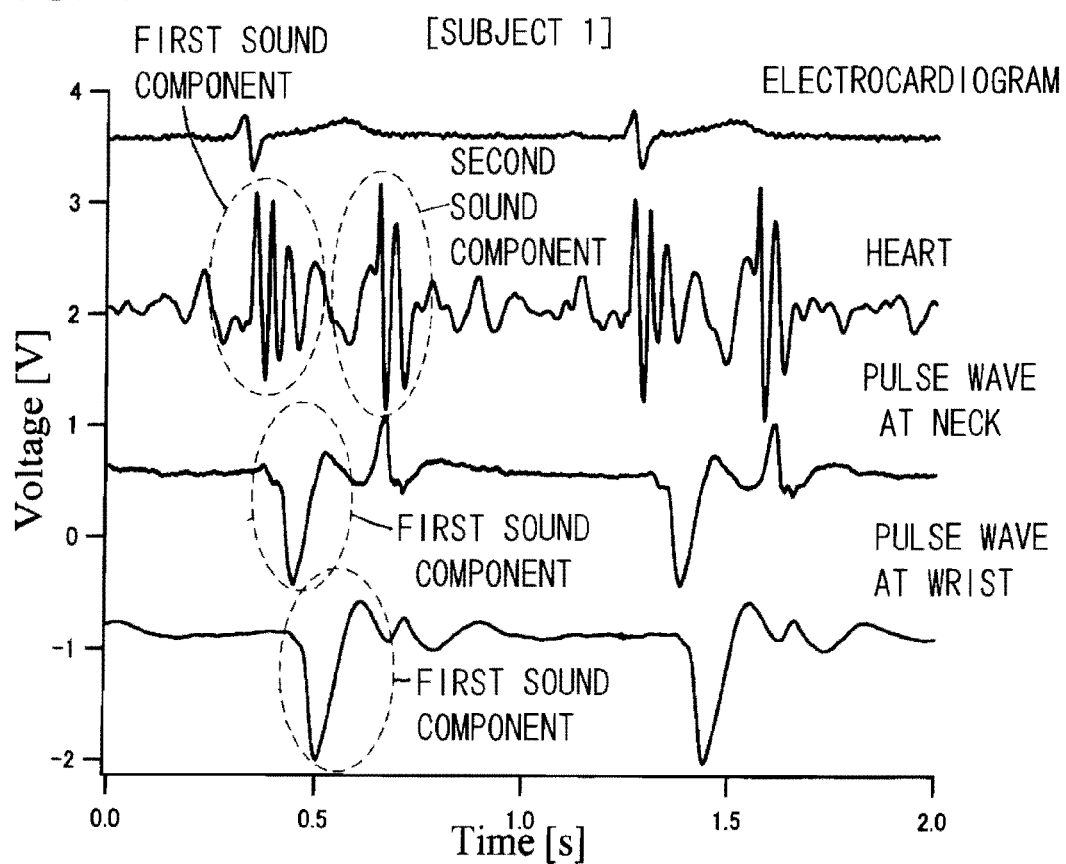
FIG. 4 illustrates waveforms of an electrocardiogram, heart sounds, pulse waves at the neck and pulse waves at a wrist with respect to a subject 1.

FIGS. 4 to 8 illustrate the result of a diagnosis on the subject 1, whose age is 23, that was made by employing signal processing in the above diagnostic method. FIG. 4 illustrates detection signals (voltages) synchronously detected by the three piezoelectric transducers 1 to 3 and the electrocardiograph 4. That is, FIG. 4 shows an electrocardiogram, heart sounds, pulse waves at the neck, and pulse waves at the wrist. Each of the heart sounds contains a first sound component accompanying systole and a second sound component accompanying diastole. However, each of the pulse waves at the wrist contains only the first sound component, and substantially does not contain the second sound component.

Figure 5:
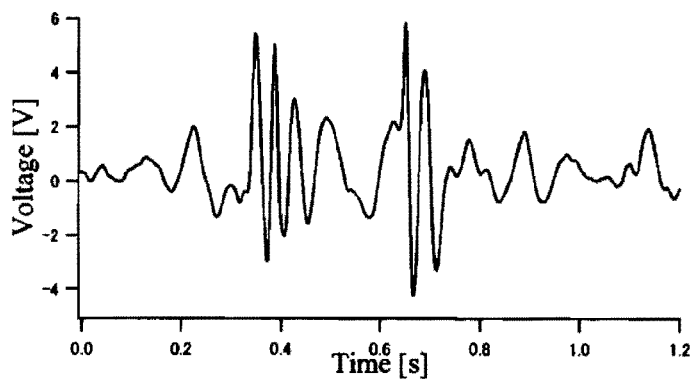
FIG. 5(a) shows a heart sound of the subject 1 in a raw waveform.
FIG. 5(b) shows a heart sound of the subject 1 in a waveform of the first sound component extracted by using a window function.
FIG. 5(c) shows a heart sound of the subject 1 in a waveform of a signal into which the extracted first sound component was frequency-converted.
Figure 5:
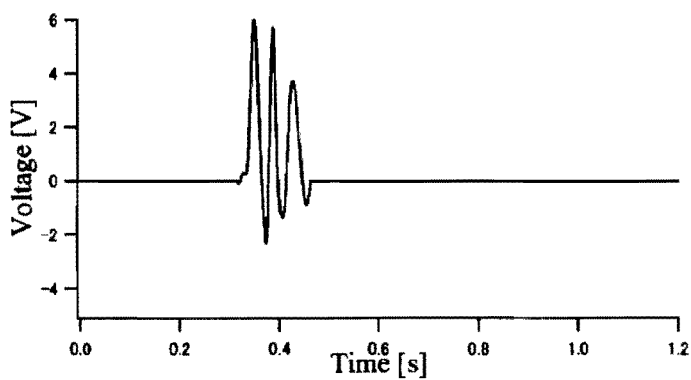
Figure 5:
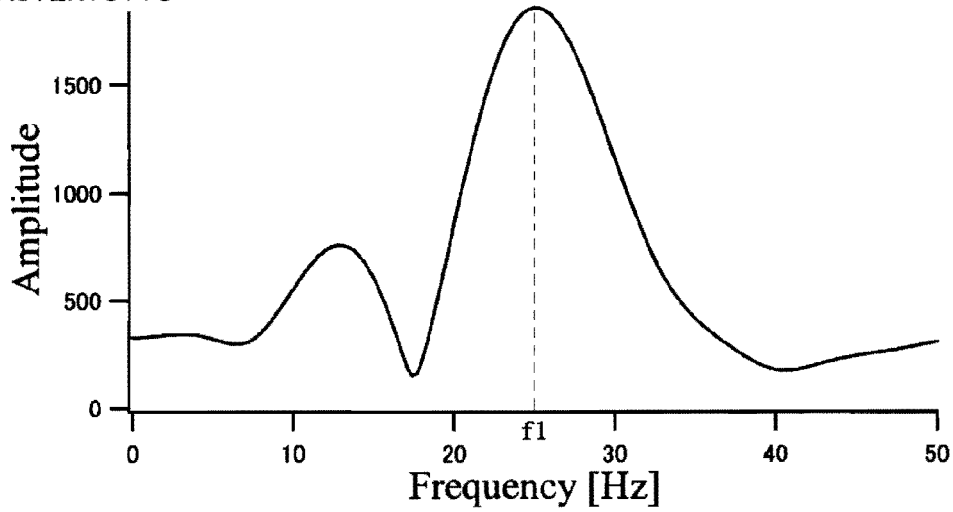

FIG. 5 generally shows a heart sound. Specifically, FIGS. 5(a) to 5(c) illustrate a raw waveform, a waveform of the first sound component that was extracted by using a window function, and a signal into which the extracted first sound component was frequency-converted, respectively. The peak frequency f1 of the first sound component in the heart sound was 25 Hz.

Figure 6:
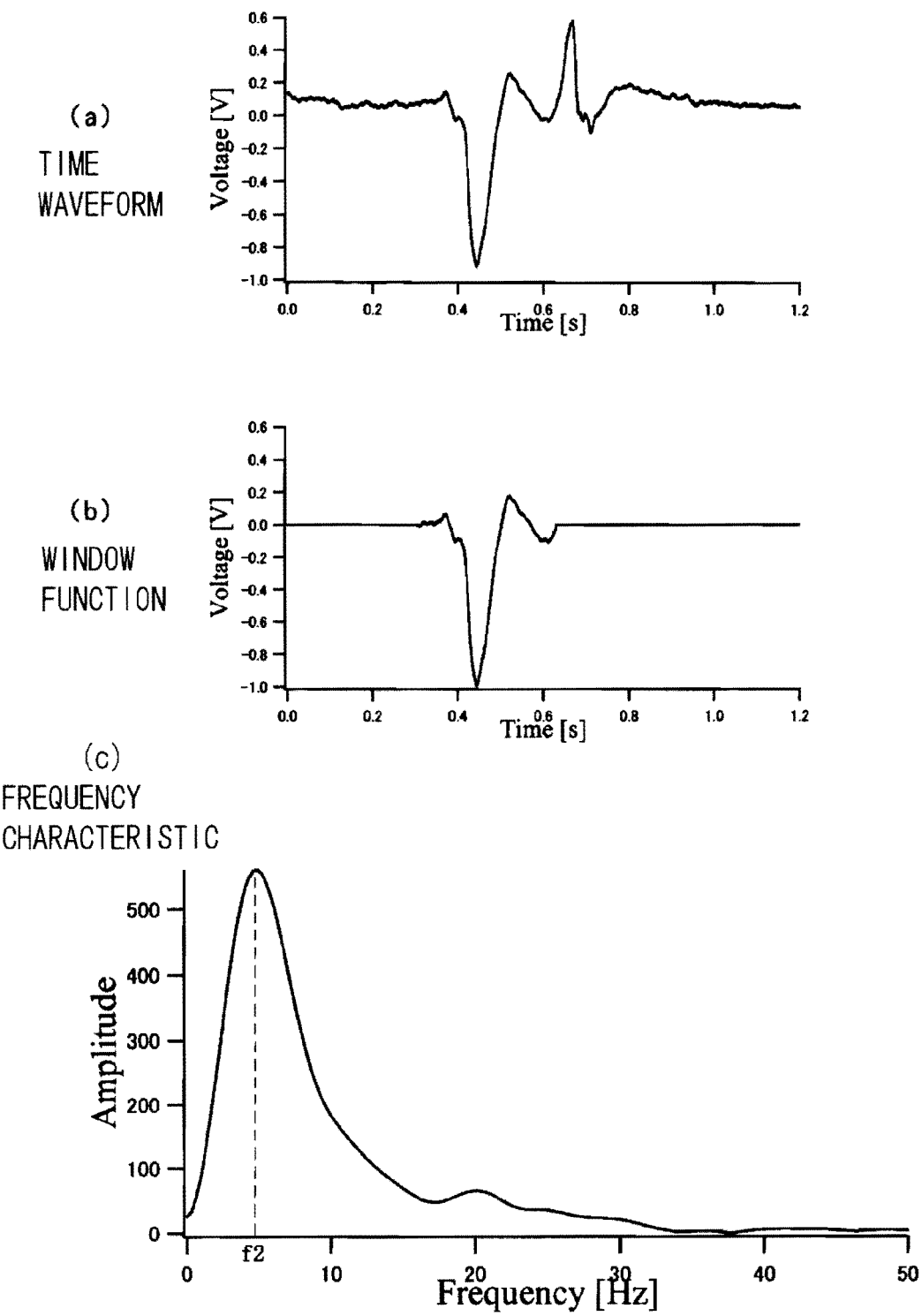
FIG. 6(a) shows a pulse wave at the neck of the subject 1 in raw waveform.
FIG. 6(b) shows a pulse wave at the neck of the subject 1 in a waveform of the first sound component extracted by using a window function.
FIG. 6(c) shows a pulse wave at the neck of the subject 1 in a waveform of a signal into which the extracted first sound component was frequency-converted.

FIG. 6 generally shows a pulse wave at the neck. Specifically, FIGS. 6(a) to 6(c) illustrate a raw waveform, a waveform of the first sound component that was extracted by using a window function, and a signal into which the extracted first sound component was frequency-converted, respectively. The peak frequency f2 of the first sound component in the pulse wave at the neck was 4.9 Hz.

Figure 7:
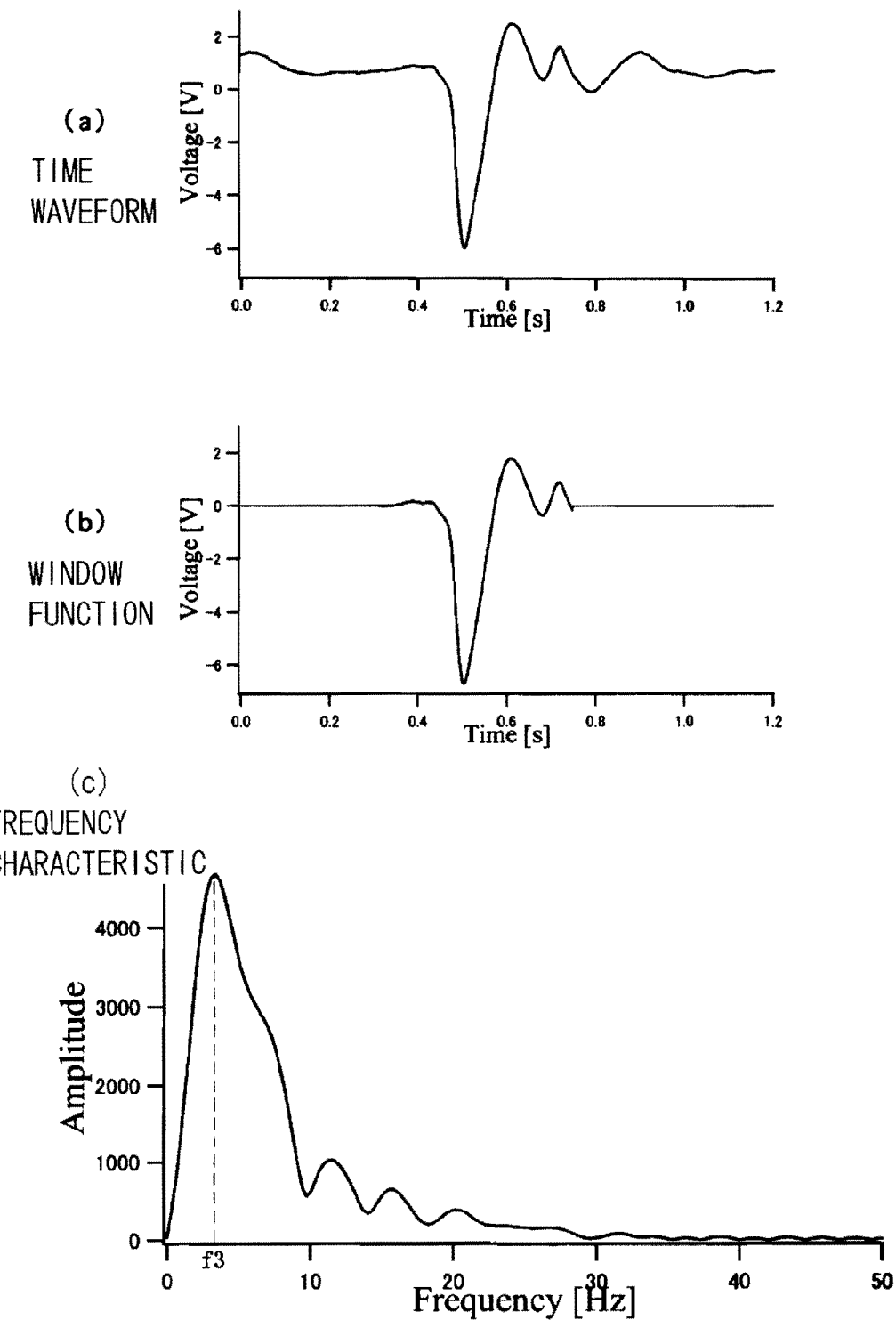
FIG. 7(a) shows a pulse wave at the wrist of the subject 1 in a raw waveform.
FIG. 7(b) shows a pulse wave at the wrist of the subject 1 in a waveform of the first sound component extracted by using a window function.
FIG. 7(c) shows a pulse wave at the wrist of the subject 1 in a waveform of a signal into which the extracted first sound component was frequency-converted.

FIG. 7 generally shows a pulse wave at the wrist. Specifically, FIGS. 7(a) to (c) illustrate a raw waveform, a waveform of the first sound component that was extracted by using a window function, and a signal into which the extracted first sound component was frequency-converted, respectively. The peak frequency f3 of the first sound component in the pulse wave at the wrist was 3.4 Hz.

Figure 8:
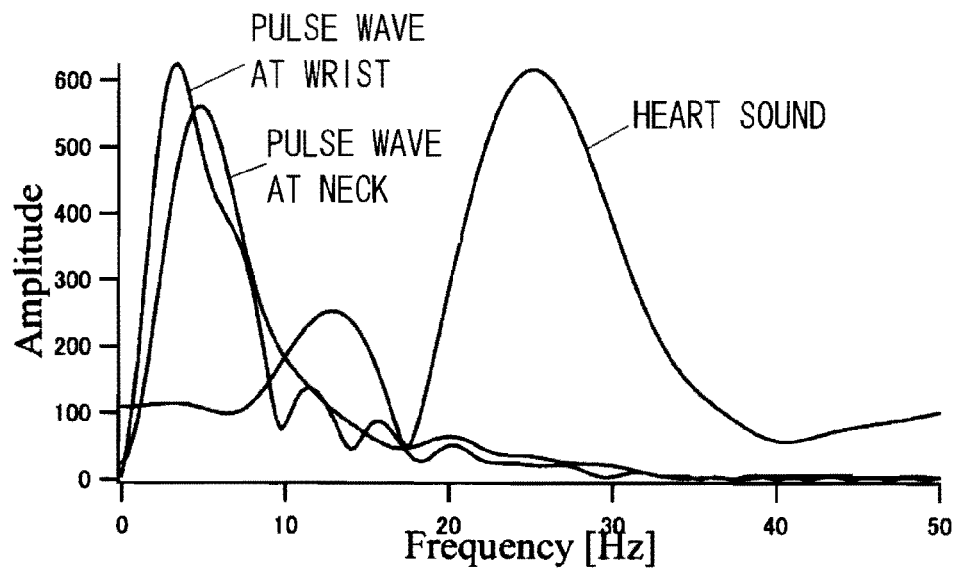
FIG. 8 illustrates frequency characteristics of the heart sound, the pulse wave at the neck, and the pulse wave at the wrist with respect to the subject 1.

FIG. 8 illustrates, in a graph, frequency characteristics of the heart sound, the pulse wave at the neck, and the pulse wave at the wrist with respect to the subject 1. The graph was obtained by normalizing the waveforms with respect to the maximum amplitudes. FIG. 8 is unique to the subject 1 and is related to the degree of the hardness of arteries. The difference between the peak frequency of the heart sound and that of the pulse wave at the neck of the subject 1 was 20.1 Hz, whereas the difference between the peak frequency of the heart sound and that of the pulse wave at the wrist was 21.6 Hz.

-- Subject 2 --

Figure 9:
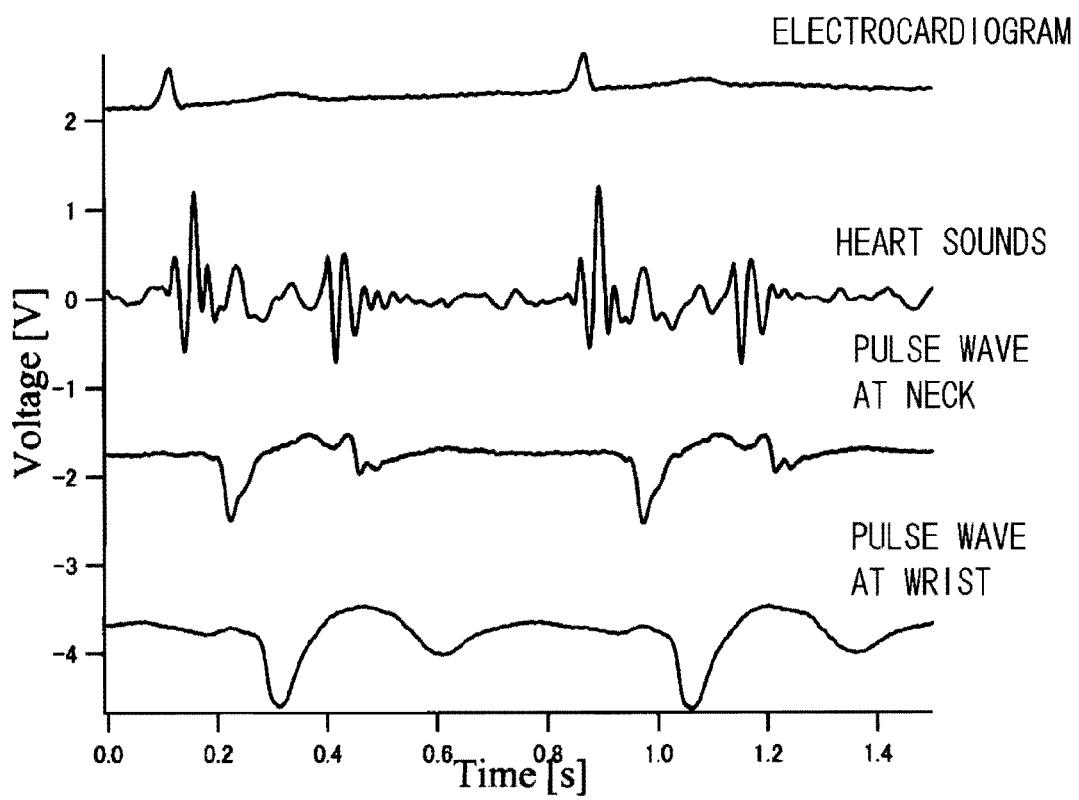
FIG. 9 illustrates waveforms of an electrocardiogram, heart sounds, pulse waves at the neck and pulse waves at a wrist with respect to a subject 2.

FIGS. 9 to 13 illustrate the result of a diagnosis on the subject 2, whose age is 23. FIG. 9 illustrates detection signals synchronously detected by the three piezoelectric transducers 1 to 3 and the electrocardiograph 4. That is, FIG. 4 shows an electrocardiogram, heart sounds, pulse waves at the neck, and a pulse waves at the wrist.

Figure 10:
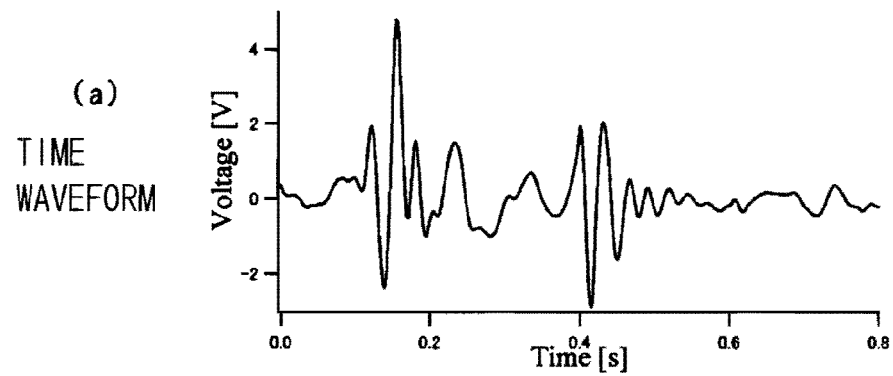
FIG. 10(a) shows a heart sound of the subject 2 in a raw waveform.
FIG. 10(b) shows a heart sound of the subject 2 in a waveform of the first sound component that was extracted by using a window function.
FIG. 10(c) shows a heart sound of the subject 2 in a waveform of a signal into which the extracted first sound component was frequency-converted.
Figure 10:
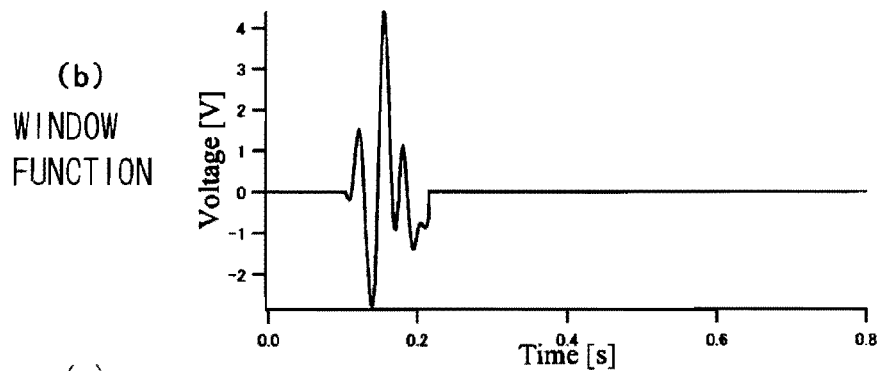
Figure 10:
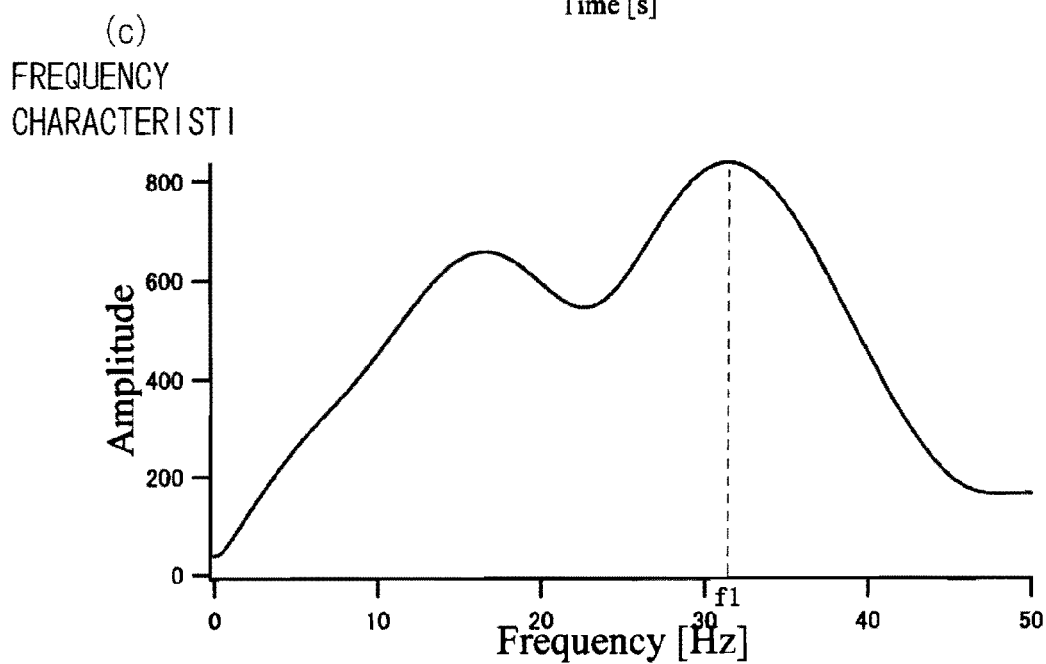

FIG. 10 generally shows a heart sound. Specifically, FIGS. 10(a) to 10(c) illustrate a raw waveform, a waveform of the first sound component that was extracted by using a window function, and a signal into which the extracted first sound component was frequency-converted, respectively. The peak frequency f1 of the first sound component in the heart sound was 31.7 Hz.

Figure 11:
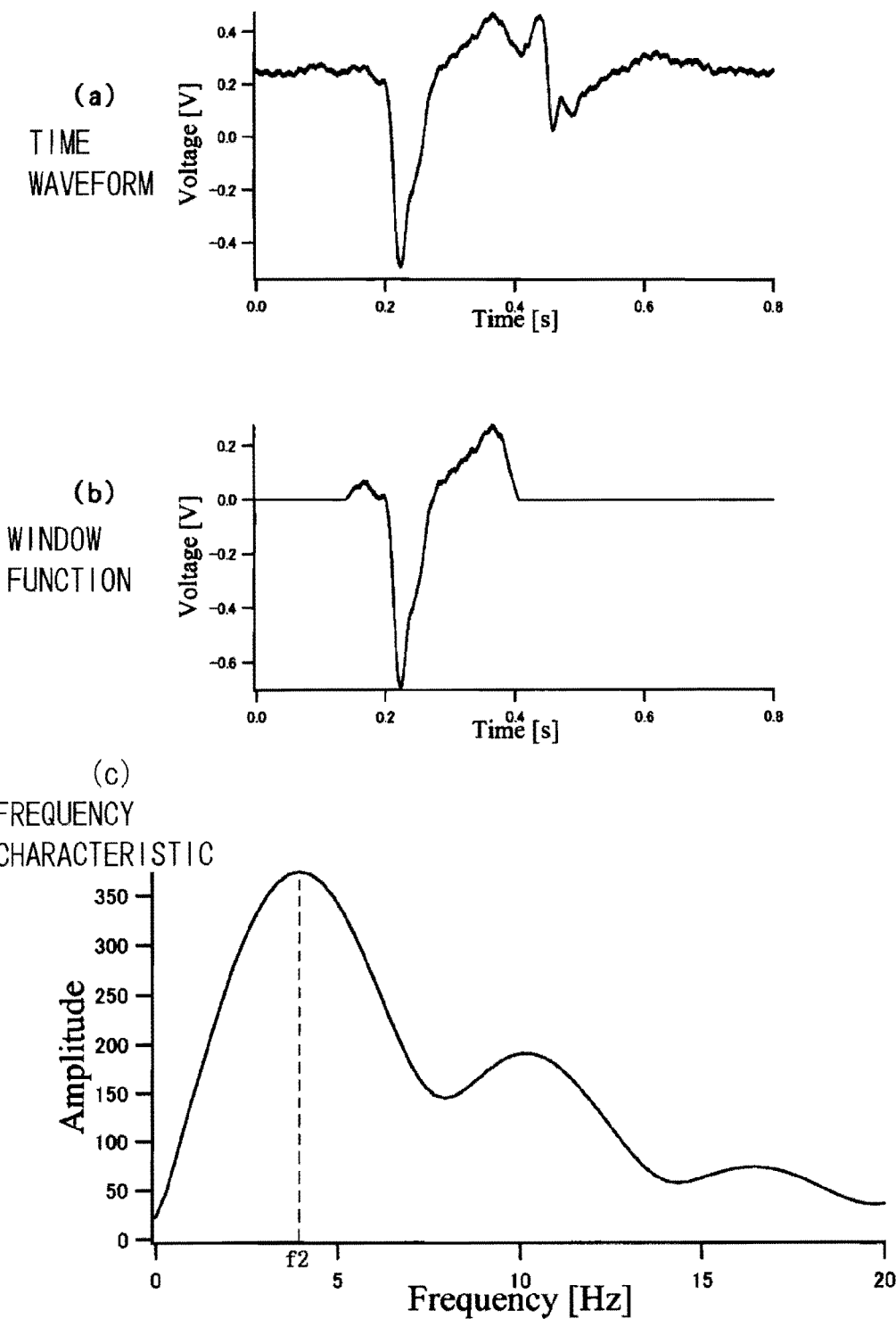
FIG. 11(a) shows a pulse wave at the neck of the subject 2 in a raw waveform.
FIG. 11(b) shows a pulse wave at the neck of the subject 2 in a waveform of the first sound component that was extracted by using a window function.
FIG. 11(c) shows a pulse wave at the neck of the subject 2 in a waveform of a signal into which the extracted first sound component was frequency-converted.

FIG. 11 generally shows a pulse wave at the neck. Specifically, FIGS. 11(a) to 11(c) illustrate a raw waveform, a waveform of the first sound component that was extracted by using a window function, and a signal into which the extracted first sound component was frequency-converted, respectively. The peak frequency f2 of the first sound component in the pulse wave at the neck was 4.3 Hz.

Figure 12:
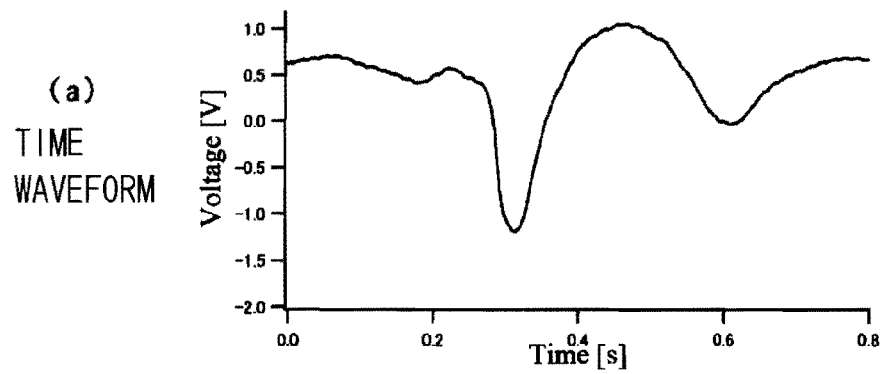
FIG. 12(a) shows a pulse wave at the wrist of the subject 2 in a raw waveform.
FIG. 12(b) shows a pulse wave at the wrist of the subject 2 in a waveform of the first sound component that was extracted by using a window function.
FIG. 12(c) shows a pulse wave at the wrist of the subject 2 in a waveform of a signal into which the extracted first sound component was frequency-converted.
Figure 12:
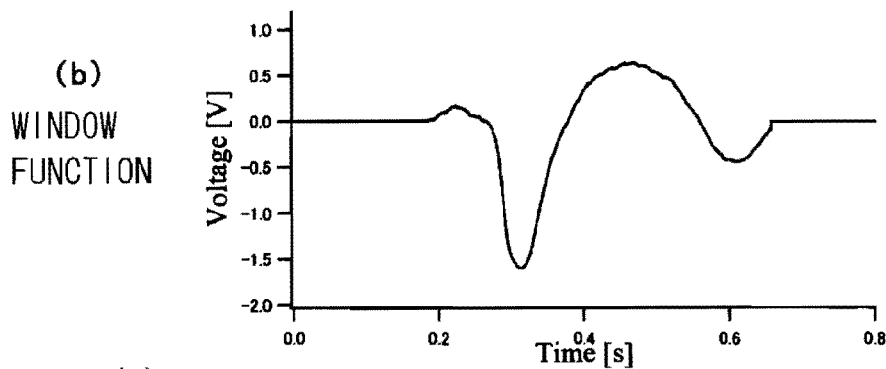
Figure 12:
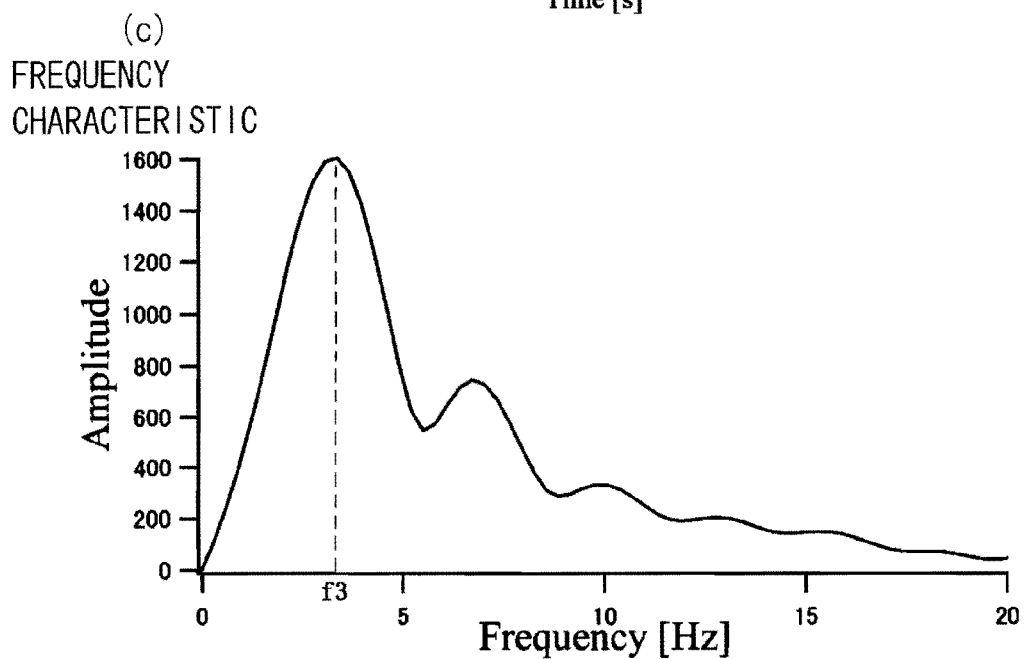

FIG. 12 generally shows a pulse wave at the wrist. Specifically, FIGS. 12(a) to 12(c) illustrate a raw waveform, a waveform of the first sound component that was extracted by using a window function, and a signal into which the extracted first sound component was frequency-converted, respectively. The peak frequency f3 of the first sound component in the pulse wave at the wrist was 3.4 Hz.

Figure 13:
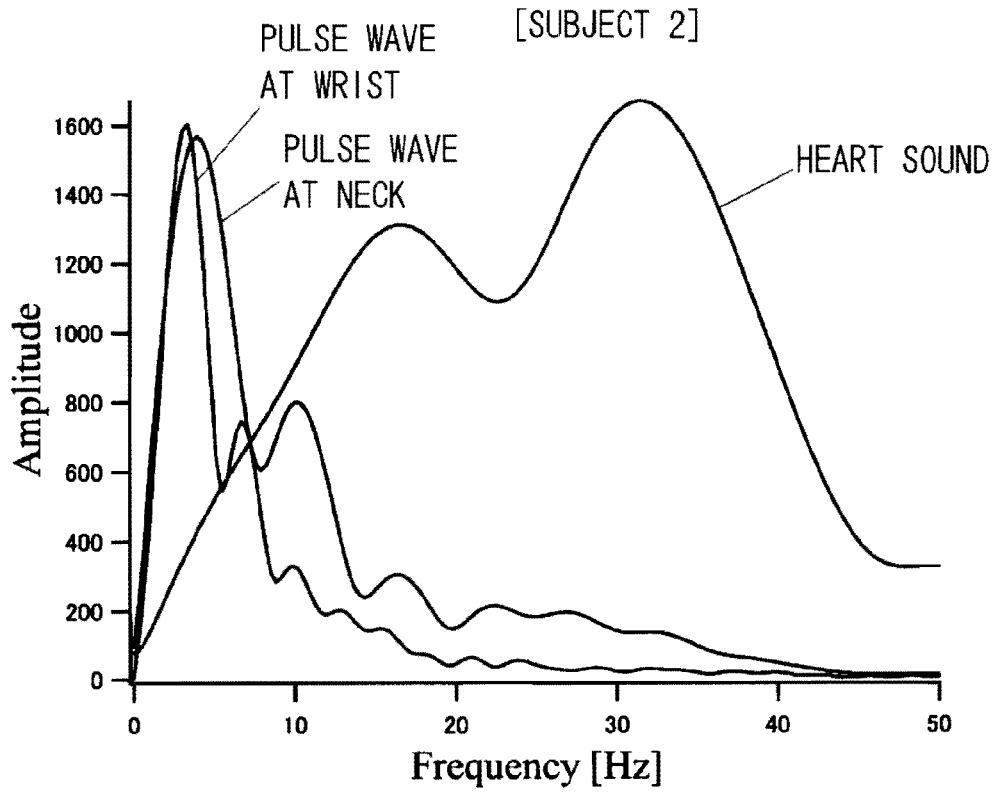
FIG. 13 illustrates frequency characteristics of the heart sound, the pulse wave at the neck, and the pulse wave at the wrist with respect to the subject 2.

FIG. 13 illustrates, in a graph, frequency characteristics of the heart sound, the pulse wave at the neck, and the pulse wave at the wrist with respect to the subject 2. The graph was obtained by normalizing the waveforms with respect to the maximum amplitudes. In the case of the subject 2, the difference between the peak frequency of the heart sound and that of the pulse wave at the neck was 27.4 Hz, whereas the difference between the peak frequency of the heart sound and that of the pulse wave at the wrist was 28.3 Hz.

-- Subject 3 --

Figure 14:
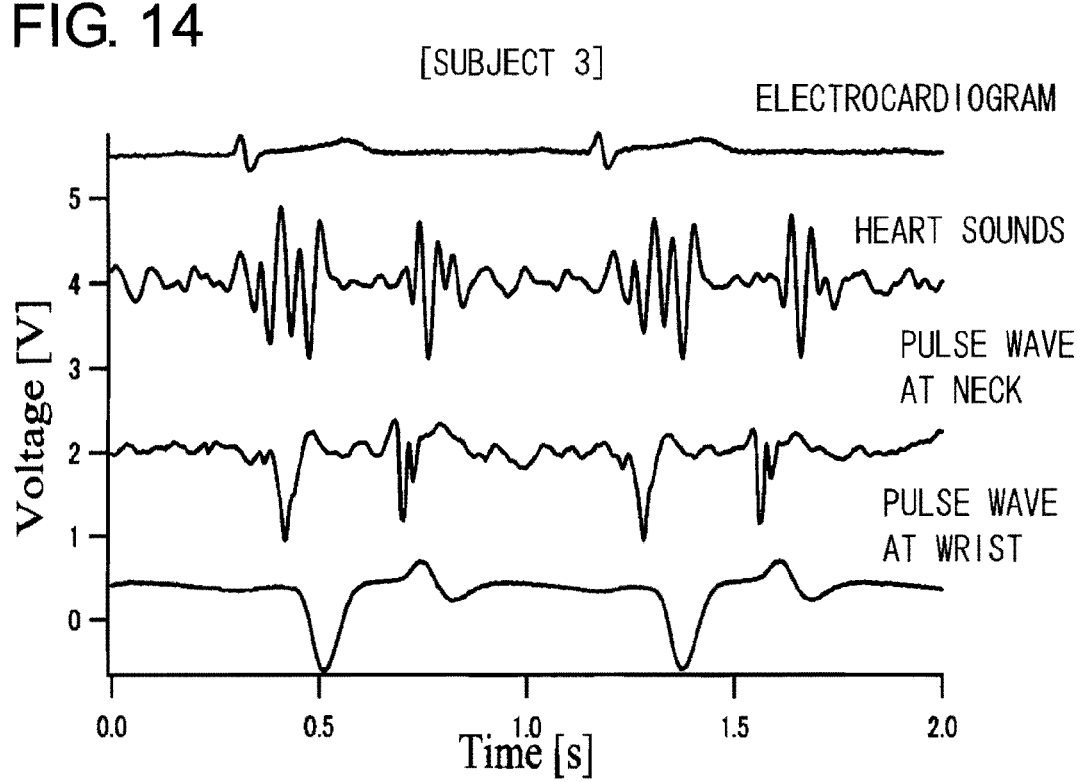
FIG. 14 illustrates waveforms of an electrocardiogram, heart sounds, pulse waves at the neck and pulse waves at a wrist with respect to a subject 3.

FIGS. 14 to 18 illustrate the result of a diagnosis on the subject 3, whose age is 60. FIG. 14 illustrates detection signals (voltages) synchronously detected by the three piezoelectric transducers 1 to 3 and the electrocardiograph 4. That is, FIG. 14 shows an electrocardiogram, heart sounds, pulse waves at the neck, and pulse waves at the wrist.

Figure 15:
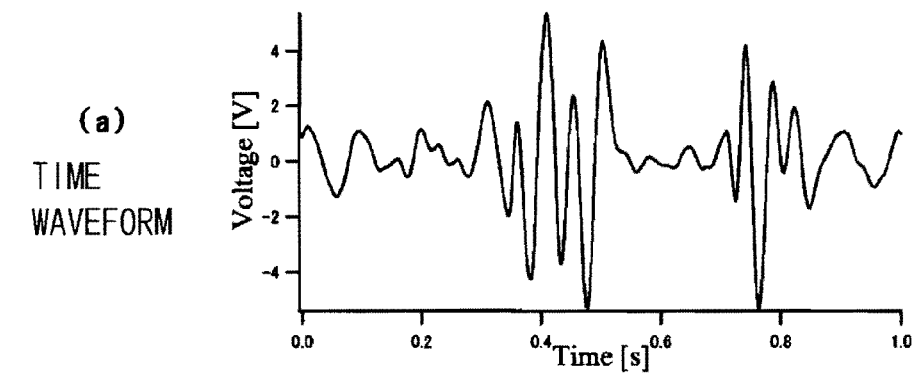
FIG. 15(a) shows a heart sound of the subject 3 in a raw waveform.
FIG. 15(b) shows a heart sound of the subject 3 in (a waveform of the first sound component extracted by using a window function.
FIG. 15(c) shows a heart sound of the subject 3 in a waveform of a signal into which the extracted first sound component was frequency-converted.
Figure 15:
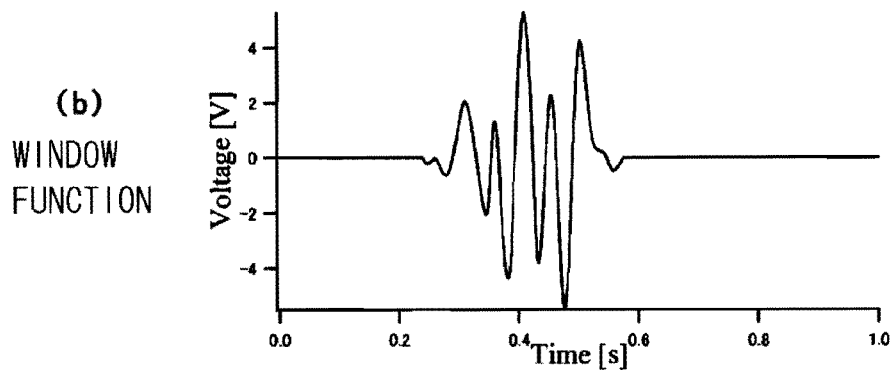
Figure 15:
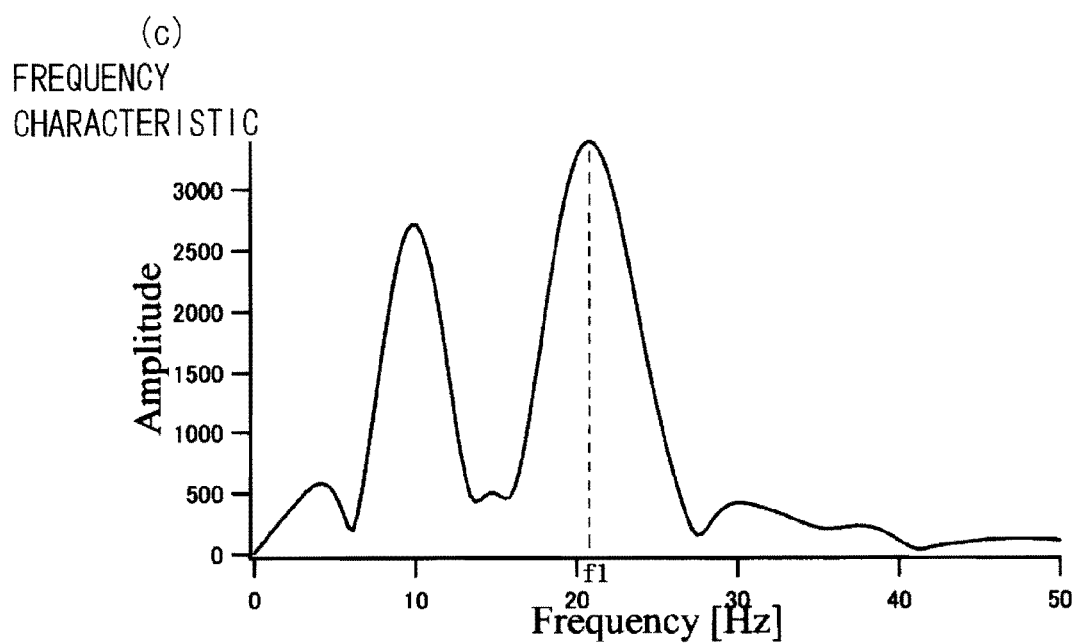

FIG. 15 generally shows a heart sound. Specifically, FIGS. 15(a) to 15(c) illustrate a raw waveform, a waveform of the first sound component that was extracted by using a window function, and a signal into which the extracted first sound component was frequency-converted, respectively. The peak frequency f1 of the first sound component in the heart sound was 21.1 Hz.

Figure 16:
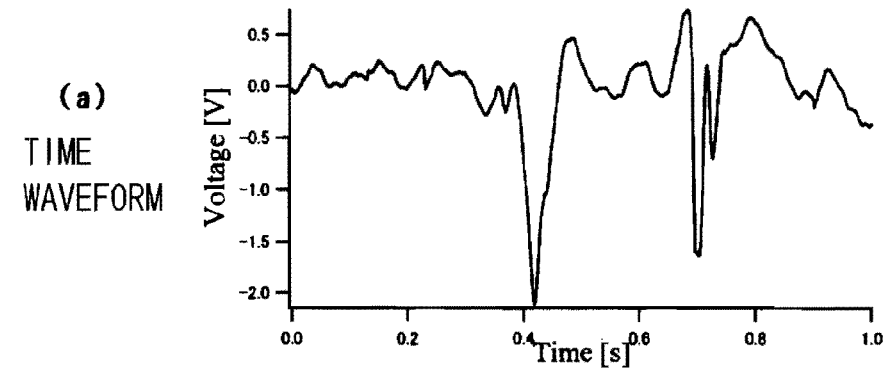
FIG. 16(a) shows a pulse wave at the neck of the subject 3 in a raw waveform.
FIG. 16(b) shows a pulse wave at the neck of the subject 3 in a waveform of the first sound component extracted by using a window function.
FIG. 16(c) shows a pulse wave at the neck of the subject 3 in a waveform of a signal into which the extracted first sound component was frequency-converted.
Figure 16:
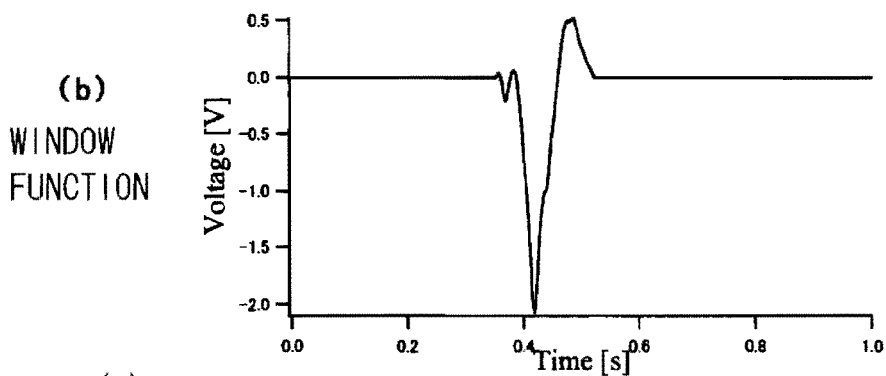
Figure 16:
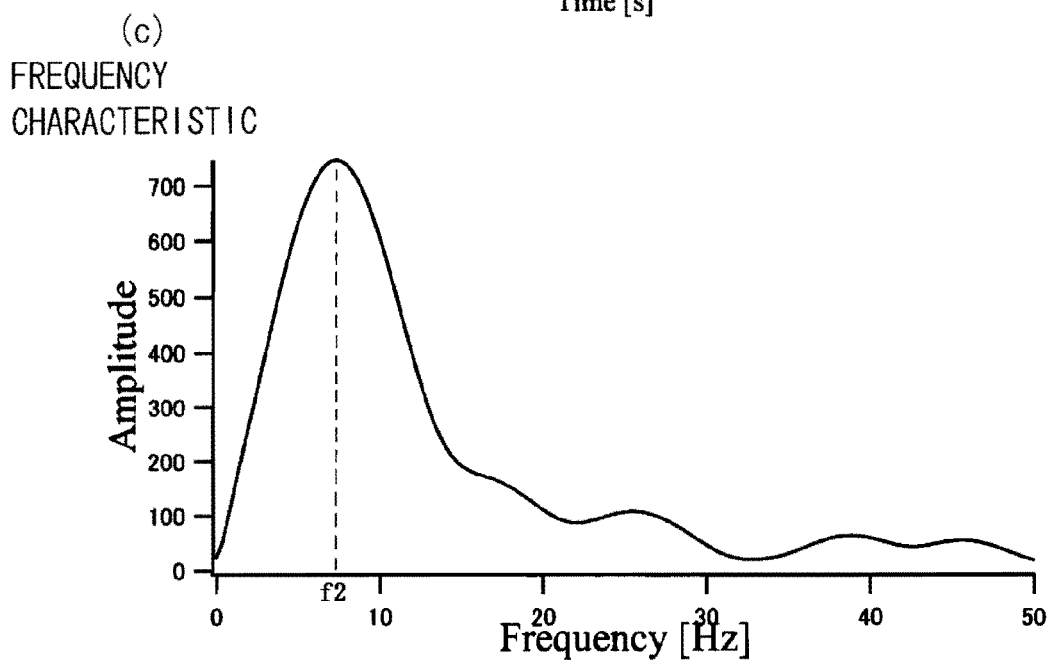

FIG. 16 generally shows a pulse wave at the neck. Specifically, FIGS. 16(a) to 16(c) illustrate a raw waveform, a waveform of the first sound component that was extracted by using a window function, and a signal into which the extracted first sound component was frequency-converted, respectively. The peak frequency f2 of the first sound component in the pulse wave at the neck was 7.3 Hz.

Figure 17:
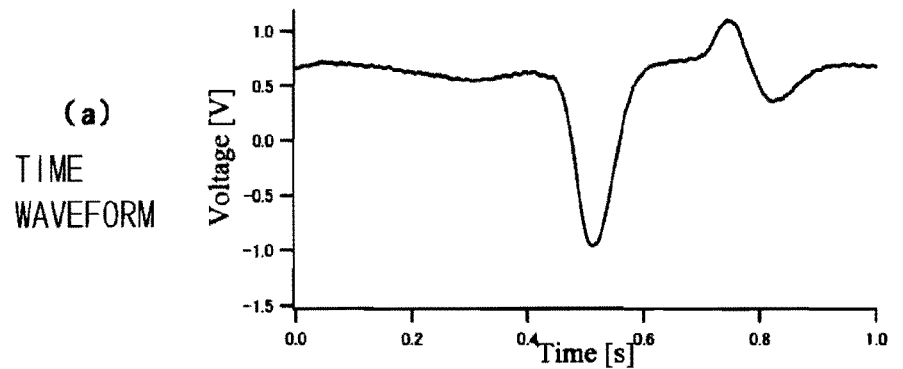
FIG. 17(a) shows a pulse wave at the wrist of the subject 3 in a raw waveform.
FIG. 17(b) shows a pulse wave at the wrist of the subject 3 in a waveform of the first sound component that was extracted by using a window function.
FIG. 17(c) shows a pulse wave at the wrist of the subject 3 in a waveform of a signal into which the extracted first sound component was frequency-converted.
Figure 17:
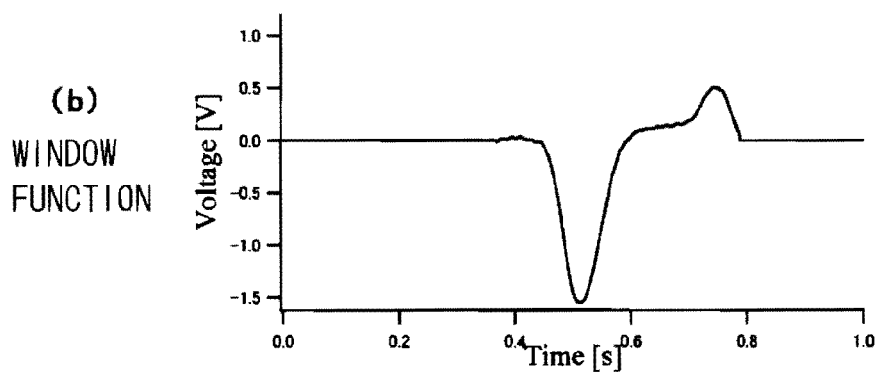
Figure 17:
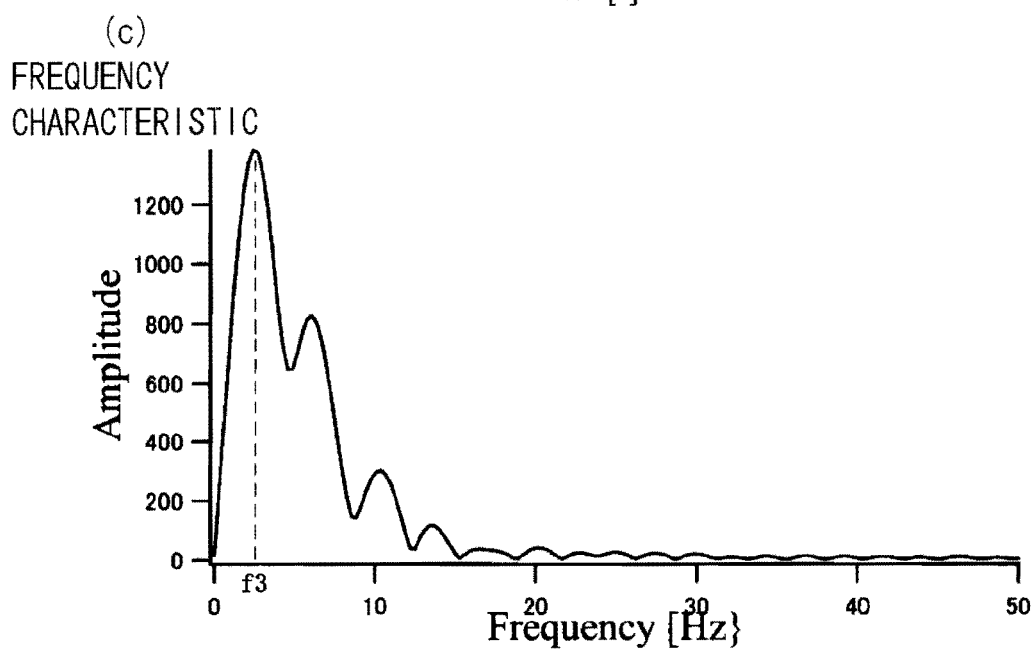

FIG. 17 generally shows a pulse wave at the wrist. FIGS. 17(a) to 17(c) illustrate a raw waveform, a waveform of the first sound component that was extracted by using a window function, and a signal into which the extracted first sound component was frequency-converted, respectively. The peak frequency f3 of the first sound component in the pulse wave at the wrist was 2.4 Hz.

Figure 18:
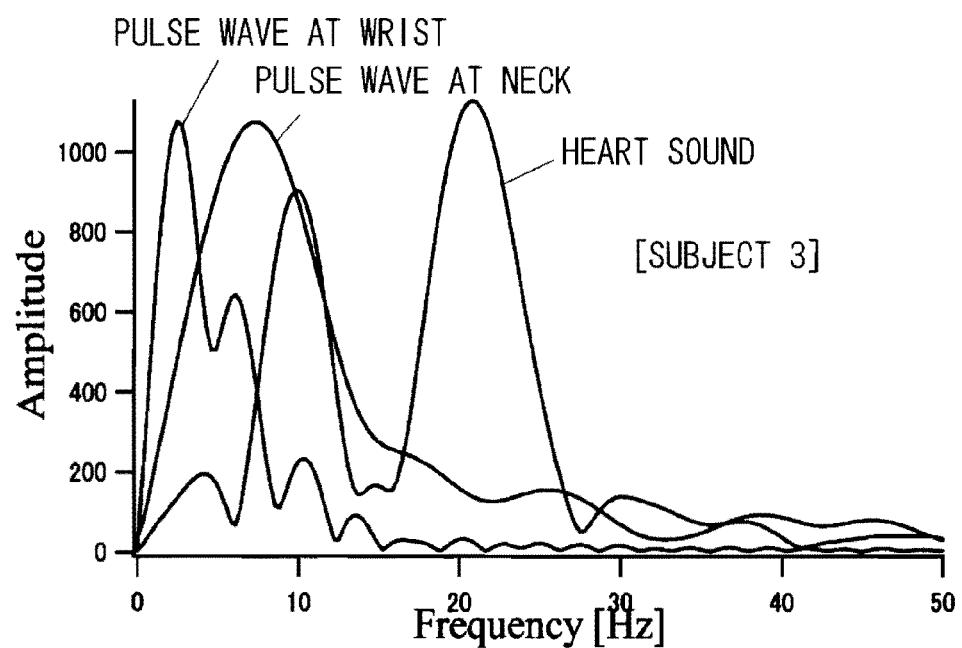
FIG. 18 illustrates frequency characteristics of the heart sound, the pulse wave at the neck, and the pulse wave at the wrist with respect to the subject 3.

FIG. 18 illustrates, in a graph, frequency characteristics of the heart sound, the pulse wave at the neck, and the pulse wave at the wrist with respect to the subject 3. The graph was obtained by normalizing the waveforms with respect to the maximum amplitudes. In the case of the subject 3, the difference between the peak frequency of the heart sound and that of the pulse wave at the neck was 13.8 Hz, whereas the difference between the peak frequency of the heart sound and that of the pulse wave at the wrist was 18.7 Hz. As is evident from comparison with the subjects 1 and 2, both the frequency differences are small. In particular, it is clear that the difference between the peak frequency of the heart sound and that of the pulse wave at the neck is markedly small.

The following table shows comparisons of the peak frequencies and of the frequency differences among the subjects 1, 2, and 3 obtained from FIGS. 8, 13, and 18. The unit is Hz.

TABLE 1

| | Peak Frequency | | | Peak Frequency Difference | | |
|---|---|---|---|---|---|---|
| | Heart Sound | Neck | Wrist | Heart Sound - Neck | Heart Sound - Wrist | Neck - Wrist |
| Subject 1 | 25.0 | 4.9 | 3.4 | 20.1 | 21.6 | 1.5 |
| Subject 2 | 31.7 | 4.3 | 3.4 | 27.4 | 28.3 | 0.9 |
| Subject 3 | 21.1 | 7.3 | 2.4 | 13.8 | 18.7 | 4.9 |

As is clearly shown from Table 1, the peak frequency differences for the elderly subject 3 are smaller than those for the young subjects 1 and 2. That is, in the case of the subjects 1 and 2, who are deemed to have little arteriosclerosis, the viscoelasticity of the arterial walls is high, so the peak frequency differences are larger. In contrast, in the case of the subject 3, who is deemed to have advanced arteriosclerosis, the peak frequency differences are relatively small. In this way, it is possible to estimate the degree of arteriosclerosis on the basis of the extent of a peak frequency difference.

In the case of the subject 3, the difference between the peak frequency of the heart sound and that of the pulse wave at the neck is considerably smaller than the difference between the peak frequency of the heart sound and that of the pulse wave at the wrist. In other words, the difference between the peak frequency of the pulse wave at the neck and that at the wrist of the subject 3 is significantly larger than those of the subjects 1 and 2. This may result from a cause lying in an artery connecting the heart and the carotid artery in the neck, such as hardening of the artery. In this way, not only the difference between the peak frequency of a heart sound and that of a pulse wave but also the difference between the peak frequencies of pulse waves in at least two locations of a human body can be used in diagnosis of, for example, arteriosclerosis.

In the foregoing description, an example is described in which the degree of arteriosclerosis is determined on the basis of the difference between the peak frequency of a heart sound and that of a pulse wave or the difference between the peak frequencies of pulse waves. Alternatively, the degree of arteriosclerosis can also be determined on the basis of the ratio between the peak frequency of a pulse wave and that of a heart sound. The peak frequency ratio R1 can be calculated by the following:

$$R1 = f2/f1,$$

where f1 is the peak frequency of the heart sound, and f2 is the peak frequency of the pulse wave.

Typically, the peak frequency ratio R1 has a value being smaller than one, and it is nearer to one for individuals having a higher degree of arteriosclerosis.

In addition, the overall degree of arteriosclerosis of a subject may also be estimated by finding the ratio between the peak frequency of a heart sound and each of the peak frequencies of pulse waves at two different locations (e.g., a wrist and an ankle). In this case, the peak frequency ratio R2 may be found by the following expression:

$$R2 = (f1 - f3)/(f1 - f2),$$

where f1 is the peak frequency of the heart sound (the first sound component), f2 is the peak frequency of the pulse wave at the wrist, and f3 is the peak frequency of the pulse wave at the ankle.

This peak frequency ratio R2 is related to the frequency difference in the section from the heart to the ankle and that in the section from the heart to the wrist. Accordingly, the evaluation of the peak frequency ratio R2 enables the estimation of the degree of the progress of arteriosclerosis of the entire body.

The detection means can be made to come into contact with a human body by any process, including incorporating it into clothes, watches, rings, or jewelry, which are worn by people in daily life, or other things that a subject can come into contact with for measurement, such as a chair, sofa, blanket, or shoe. The use of such a process makes it possible to obtain data on a regular basis without causing a subject to become aware of measurement. Accordingly, the device can be used as a home-use measuring instrument to continuously store measured data.

Although a limited number of embodiments are described herein, one of ordinary skill in the art will readily recognize that there could be variations to any of these embodiments and those variations would be within the scope of the appended claims. Thus, it will be apparent to those skilled in the art that various changes and modifications can be made to the communication system described herein without departing from the scope of the appended claims and their equivalents.

The invention claimed is:

1. An arteriosclerosis diagnostic device comprising:
   first detection module to detect a heart sound;
   second detection module to detect a pulse wave in at least one location of a living body, the pulse wave propagating through an artery in relation to the heart sound;
   converter module to convert detection signals detected by the first and second detection modules into their respective frequency signals; and
   determining module to determine the degree of arteriosclerosis by comparing the frequency signal of the heart sound and the frequency signal of the pulse wave.

2. The arteriosclerosis diagnostic device according to claim 1, further comprising an extracting module to extract only the first sound component accompanying systole from the detection signals detected by the first and the second detection modules by using a window function.

3. The arteriosclerosis diagnostic device according to claim 1, wherein the determining module to determine the degree of arteriosclerosis includes:
   peak-frequency determining module to specify a peak frequency or a center frequency of each of the frequency signals; and
   comparing module to determine the degree of arteriosclerosis by comparing the peak frequencies or the center frequencies of the frequency signals.

4. The arteriosclerosis diagnostic device according to claim 3, wherein the determining module to determine the degree of arteriosclerosis determines the degree of arteriosclerosis on the basis of a difference between the peak frequency or the center frequency of one of the frequency signals and the peak frequency or the center frequency of another of the frequency signals.

5. The arteriosclerosis diagnostic device according to claim 3, wherein the determining module to determine the degree of arteriosclerosis determines the degree of arteriosclerosis on the basis of a ratio of the peak frequency or the center frequency of one of the frequency signals to the peak frequency or the center frequency of another of the frequency signals.

6. The arteriosclerosis diagnostic device according to claim 3, wherein the determining module to determine the degree of arteriosclerosis determines the degree of arteriosclerosis on the basis of a ratio of a difference between the peak frequency or the center frequency of the heart sound and the peak frequency or the center frequency of the pulse wave at a first location of a living body to a difference between the peak frequency or the center frequency of the heart sound and the peak frequency or the center frequency of the pulse wave at a second location different from the first location.

7. The arteriosclerosis diagnostic device according to claim 1, wherein each of the first and second detection modules is a piezoelectric transducer.

8. The arteriosclerosis diagnostic device according to claim 2, wherein the determining module to determine the degree of arteriosclerosis includes:
   peak-frequency determining module to specify a peak frequency or a center frequency of each of the frequency signals; and
   comparing module to determine the degree of arteriosclerosis by comparing the peak frequencies or the center frequencies of the frequency signals.

9. The arteriosclerosis diagnostic device according to claim 8, wherein the determining module to determine the degree of arteriosclerosis determines the degree of arteriosclerosis on the basis of a difference between the peak frequency or the center frequency of one of the frequency signals and the peak frequency or the center frequency of another of the frequency signals.

10. The arteriosclerosis diagnostic device according to claim 8, wherein the determining module to determine the degree of arteriosclerosis determines the degree of arteriosclerosis on the basis of a ratio of the peak frequency or the center frequency of one of the frequency signals to the peak frequency or the center frequency of another of the frequency signals.

11. The arteriosclerosis diagnostic device according to claim 8, wherein the determining module to determine the degree of arteriosclerosis determines the degree of arteriosclerosis on the basis of a ratio of a difference between the peak frequency or the center frequency of the heart sound and the peak frequency or the center frequency of the pulse wave at a first location of a living body to a difference between the peak frequency or the center frequency of the heart sound and the peak frequency or the center frequency of the pulse wave at a second location different from the first location.

* * * * *